United States Patent
Kempf et al.

(10) Patent No.: US 6,747,175 B2
(45) Date of Patent: Jun. 8, 2004

(54) CHLORINATION OF AN ANILINE IN A HYDROFLUORIC MEDIUM

(75) Inventors: Hubert Kempf, Salindres (FR); Gilbert Guidot, Massanes (FR); Laurent Saint-Jalmes, Meyzieu (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/204,942

(22) PCT Filed: Feb. 28, 2001

(86) PCT No.: PCT/FR01/00578

§ 371 (c)(1),
(2), (4) Date: Oct. 21, 2002

(87) PCT Pub. No.: WO01/64623

PCT Pub. Date: Sep. 7, 2001

(65) Prior Publication Data

US 2003/0130542 A1 Jul. 10, 2003

(30) Foreign Application Priority Data

Mar. 1, 2000 (FR) .......................................... 00 02628

(51) Int. Cl.$^7$ ...................... C07C 209/74; C07D 231/12
(52) U.S. Cl. ...................... 564/412; 564/442; 548/343.1
(58) Field of Search ................................ 564/412, 442; 548/343.1

(56) References Cited

U.S. PATENT DOCUMENTS

| | | | | |
|---|---|---|---|---|
| 4,748,277 A | | 5/1988 | Debois | ........................ 564/412 |
| 4,766,243 A | * | 8/1988 | Fifolt | ........................ 564/414 |
| 5,145,958 A | | 9/1992 | Kissener | ........................ 544/106 |
| 5,471,002 A | | 11/1995 | Appel | ........................ 564/412 |

* cited by examiner

*Primary Examiner*—Brian J. Davis

(57) ABSTRACT

The invention concerns a method for the synthesis of chlorinated aniline on the ring and comprising at least a sp3 hybridization carbon atom both perhalogenated and bearing a fluorine atom. Said method is characterized in that it comprises a step which consists in chlorinating a precursor aniline of said chlorinated aniline, said chlorination being carried out in a hydrofluoric medium capable of exchanging chlorine and fluorine in benzyl position. The invention is useful for the synthesis of organofluorinated and/or chlorinated compounds.

9 Claims, No Drawings

CHLORINATION OF AN ANILINE IN A HYDROFLUORIC MEDIUM

This application is an application under 35 U.S.C. Section 371 of International Application No. PCT/FR01/00578 filed on Feb. 28, 2001.

The present invention is targeted at a process for the synthesis of an aniline which is chlorinated on the ring and which comprises at least one carbon atom of $sp^3$ hybridization which is both perhalogenated and the carrier of a fluorine atom. It is targeted more particularly at the chlorination in a hydrofluoric acid medium of a precursor aniline of said chlorinated aniline.

Fluorinated molecules are playing an increasing role in pharmaceuticals and in agrochemicals. The synthesis of fluorinated derivatives is often problematic as direct fluorination reactions are generally too violent and too selective to be able to be employed. Consequently, the synthesis of fluorinated derivatives often makes use of exchanges of various substituents with fluorine and in particular exchanges of heavier halogens with fluorine.

The most widely used and the least expensive reactant in carrying out the exchange is unquestionably liquid-phase hydrofluoric acid.

Hydrofluoric acid exhibits various properties which depart from the ordinary and renders the reactions carried out within a hydrofluoric acid medium difficult to predict and in any case different from the results obtained with conventional techniques.

In particular, liquid hydrofluoric acid is a particularly aggressive medium and where numerous combinations by hydrogen bonding take place; moreover, hydrofluoric acid forms, with amines and in particular with weak amines and with aromatic heterocycles, extremely stable complexes which it is difficult to treat and to restore the free amine and the hydrofluoric acid.

Generally, an aniline bonds with four molecules of hydrofluoric acid which it will be necessary to neutralize to release the amine.

This neutralization is particularly expensive and leads to the discharging of hydrofluoric acid salts, the discharge of which is generally strictly regulated.

Currently, the chlorination of anilines takes place on the free aniline, in particular when the ring carrying the amine functional group is depleted in electrons by electron-withdrawing groups.

The hydrochloric acid given off by the chlorination of the aniline subsequently has to be neutralized to release the amine.

The problem is particularly acute in the case of anilines which carry, on a side chain, a perhalogenated and in particular perfluorinated carbon of $sp^3$ hybridization.

For this reason, one of the aims of the present invention is to provide a process which comprises a stage of chlorine/fluorine exchange in a hydrofluoric acid medium (with or without diluent) and which makes it possible to avoid a twofold release of the aniline, once from hydrofluoric acid and another time from hydrochloric acid.

Another aim of the present invention is to provide a process which makes possible good recovery of hydrofluoric acid bonded to anilines.

Another aim of the present invention is to provide a process of the preceding type which makes it possible to limit the saline discharges from the process.

These aims and others which will become apparent subsequently are achieved by means of the process for the synthesis of an aniline which is chlorinated on the ring and which comprises at least one carbon atom of $sp^3$ hybridization which is both perhalogenated and the carrier of a fluorine atom, characterized in that it comprises the stage of chlorination of a precursor aniline of the chlorinated aniline, this reaction being carried out in a hydrofluoric acid medium capable of exchanging chlorine and fluorine in the benzyl position or on a carbon carrying a chalcogen.

The term "perhalogenated carbon" should be understood as meaning a carbon of $sp^3$ nature which does not carry hydrogen and which comprises, in addition to its bond with the aryl or with the chalcogen, at most 2, advantageously at most 1, radicals, all the other atoms being halogens; said radicals are advantageously chosen from electron-withdrawing groups, in particular when there are 2 of them.

The present invention is of particular use for anilines which carry an electron-withdrawing group in the position para to the amine functional group. This electron-withdrawing group is advantageously an electron-withdrawing group which exerts its effect via an inductive effect and in particular groups perhalogenated on the carbon bonded to the aromatic ring of the aniline.

The hydrofluoric acid medium can either be liquid hydrofluoric acid or a hydrofluoric acid diluted in a solvent.

This hydrofluoric acid medium can be composed simply of the amine complexed by several molecules of hydrofluoric acid, generally from 2 to 5, most often 4. Generally, the HF/aniline ratio is between 2 and 10, advantageously between 4 and 8. The upper limits have only an economic meaning.

Although the aniline can be prepared in situ by decomposition of carbamoyl fluoride, this implementation is not preferred because of the risks of emission of fluorophosgene ($COCl_2$). According to a preferred implementation, the optional "release" of the amine from its carbamoyl fluoride is carried out before carrying out the chlorination.

The solvents used are advantageously solvents known for making possible ionic chlorination (chlorination by an entity of the $Cl^+$ type).

Mention may in particular be made, among the solvents which can be used, of fluorinated derivatives and chlorinated aromatic derivatives, such as, for example, monochlorobenzenes, dichlorobenzenes or trichlorobenzenes.

According to the present invention, it is possible to carry out a monochlorination or especially a dichlorination, the monochlorination occurring ortho and the dichlorination being essentially ortho-ortho' to the aniline functional group.

The chlorination generally occurs at a temperature of between 0 and 150° C., advantageously between 20 and 120° C.

The double chlorination occurs at temperatures greater than ambient temperature and gives good results at a temperature of between 70° C. and 150° C.; the most satisfactory results are obtained between 90° C. and 140° C.

However, to obtain very good yields, it is desirable to be at a temperature greater than or equal to 100° C. (2 significant figures), preferably greater than 100° C. To further improve the yield and the selectivity, it is desirable to introduce the substrate into a reaction mass (including solvent) corresponding to the above temperature restrictions. During heating, to avoid the unfavorable effect of the intermediate temperatures below the preferred temperatures, it is even possible to envisage heating the substrate in particular and the reactants in general before introduction.

In addition, it is desirable for the chlorine to be introduced so that the medium always remains chlorinating, in other words the rate of consumption of the chlorinating agent (e.g. chlorine) is at most equal to the rate of introduction into the medium of said chlorinating agent. For example, the fact of introducing chlorine so that it is stoichiometrically in excess with respect to the desired reaction constitutes an operating parameter which improves both the yield and the selectivity. This stoichiometric excess is advantageously produced throughout virtually the entire reaction.

In order to avoid side reactions, it is desirable, as soon as sparging of chlorine ceases, to suddenly cool the reaction mixture. This cooling is advantageously carried out at least partially by the removal of the hydrofluoric acid under reduced pressure.

According to an advantageous embodiment of the reaction, the substrate and the chlorine are introduced gradually and simultaneously over a heel of solvent or of reaction mass, brought to and maintained at the favorable temperature.

The presence of Lewis acid, such as boron trifluoride, although favoring the reaction, is not necessary. The molar amount of optional Lewis acid is advantageously between $10^{-4}$ and $10^{-1}$ with respect to the substrate.

The pressure at which the reaction is carried out is advantageously either atmospheric pressure or a pressure greater than atmospheric pressure, preferably autogenous pressure.

The chlorinating agent is advantageously chlorine, which is introduced into the reaction medium advantageously in the form of a gas. This introduction is advantageously carried out by sparging into the reaction medium, this introduction preferably being carried out at a flow rate at least equal to that defined by that of the substrate multiplied by the stoichiometry of the targeted reaction (generally 2 mol of chlorine per 1 mol of substrate).

Mention should in particular be made, among the advantages of the present invention, of the saving of a reaction stage and of a neutralization stage.

A significantly lower discharge of salt and thus better respect for the environment may also be pointed out. This is because, in a hydrofluoric acid medium, hydrochloric acid is given off. It can then be used for the regeneration of the chlorine, either by the Deacon process or by electrolysis.

The hydrochloric acid, in particular for small plants, can also be used to regenerate the chlorine by reaction with a hypochlorite. However, in that case, the discharge of saline derivatives is greater than in the case of the Deacon process or of the process by electrolysis.

Another advantage of the present invention is that of making much easier the release of the aniline from its complexes with hydrofluoric acid, thus making possible better recycling of the hydrofluoric acid and an additional saving with respect to saline discharges.

This is because, during the study which led to the present invention, it was shown that a simple distillation of the acid(s) makes it possible to remove the acids bonded to the aniline thus depleted by the chlorination.

Thus, when the reaction is carried out at atmospheric pressure, the hydrochloric acid and the hydrofluoric acid pass into the gas phase from approximately 20° C. Under these conditions, the release of the aniline is virtually complete by distillation or any other means of displacing hydrofluoric acid and hydrochloric acid by passage into the vapor phase.

This release can, of course, be carried out under a pressure greater than atmospheric pressure, in which case the temperature of release of the aniline takes place at a higher temperature. It can be carried out under reduced pressure, in which case the temperature of release takes place at a lower temperature.

Thus, the chlorination of the anilines which are targeted by the present invention makes possible complete and ready release from aniline-hydrofluoric acid complexes without the production of salts.

This greater facility in releasing the aniline from its complexes with hydrofluoric acid is related, first, to the increase in the boiling point of the chlorinated aniline with respect to the unchlorinated aniline and, secondly, by a reduction in the basicity of the aniline, which, in this case, appears to weaken the hydrofluoric acid-aniline bond.

This release of the aniline is also facilitated by the greater stability of the chlorinated aniline with respect to the starting aniline before chlorination.

These advantages are particularly marked in the case of the precursor of "Fipronil", which is para-trifluoromethylaniline (PTFMA) chlorinated ortho-ortho' to the aniline functional group.

This is because, in the preceding techniques, the chlorination reaction was carried out on para-trifluoromethylaniline freed from its hydrofluoric acid.

Substrates well suited to the present invention are the substrates corresponding to the following general formula.

The substrates which can be used according to the present invention advantageously correspond to the formula:

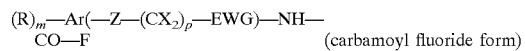

(carbamoyl fluoride form)

Or

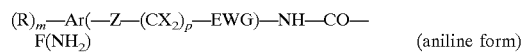

(aniline form)

where:

Ar is an aromatic ring, preferably a homocyclic ring;

the X symbols, which are alike or different, represent a fluorine or a radical of formula $C_nF_{2n+1}$ with n an integer at most equal to 5, preferably to 2;

p represents an integer at most equal to 2;

EWG represents a hydrocarbonaceous group, an electron-withdrawing group, the possible functional groups of which are inert under the reaction conditions, advantageously fluorine or a perfluorinated residue of formula $C_n F_{2n+1}$ with an integer at most equal to 8, advantageously to 5;

the total number of carbons of $—(CX_2)_p—EWG$ is advantageously between 1 and 15, preferably between 1 and 10;

m is 0 or an integer chosen within the closed range (that is to say, comprising the limits) 1 to 4;

R is a substituent which is inert under the operating conditions and which is advantageously chosen from halogens, advantageously light halogens (that is to say, chlorine and fluorine), and hydrocarbonaceous radicals, preferably alkyl, aryl, alkylchalcogenyl (such as alkyloxyl) or arylchalcogenyl (such as aryloxyl) radicals;

Z represents a single bond or a chalcogen atom, advantageously a light chalcogen atom (sulfur and oxygen).

In particular, the substrate in the aniline form can correspond to the formula:

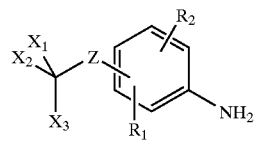

where:

Z represents a single bond or a chalcogen atom, where $X_1$, $X_2$ and sometimes $X_3$ represent alike and different halogens, with the condition that at least two halogens are other than fluorine;

$R_1$ and $R_2$ are substituents from halogens, alkyls, aryls or nitriles;

the $X_3$ radical can be an electron-withdrawing group which does not interfere with the reaction and can in particular be a perfluorinated group, denoted generally in the technical field as $R_f$.

The present invention is particularly advantageous especially for the monochlorination and dichlorination of trifluoromethylanilines and in particular for the mono- and especially dichlorination of para-trifluorochloroaniline.

It is thus particularly advantageous to use the method which has just been described above for the synthesis of ortho, ortho'-dichloro-para-trifluoro-methylaniline.

This technique opens a route to the synthesis of an N-phenylpyrazole, dichlorinated in the position ortho-ortho' to the pyrazole and carrying, in the para position, an electron-withdrawing group, advantageously a carbon atom of $sp^3$ hybridization which is both perhalogenated and the carrier of a fluorine atom, comprising a stage of chlorination of an aniline according to the invention. In the case of dichloro-para-trifluoromethylaniline, it should be mentioned that it is used in particular for preparing, by stages known per se, the insecticide known under the name of Fipronil.

The following nonlimiting examples illustrate the invention:

EXAMPLE 1

Chlorination of pTFMA (Para-Trifluoromethylaniline) in a Hydrofluoric Acid Medium The starting material is a pTFMA combined with 5.5 molecules of hydrofluoric acid. This product is liquid. The starting material and 2.2 equivalents of chlorine with respect to the pTFMA, that is to say 2.2× of moles of chlorine than there are of pTFMA, are introduced into a closed autoclave. In the closed autoclave (no degassing) with 2.2 equivalents of chlorine % pTFMA.

The results obtained are shown in the table below.

The results thus shown only measure the anilines present in the hydrofluoric acid phase. In fact, analysis of the solid or pasty residues at the bottom of the vessel which has been used as reactor shows that a good part of the ortho, ortho'-dichloro-para-trifluoromethylaniline is found in the pasty residues. So much so that the yield of dichlorinated product is much greater than that which is shown in the table!

EXAMPLE 2

Continuous Test at Atmospheric Pressure pTFMA hydrofluoride (pTFMA·6.5HF), on the one hand, and chlorine, on the other hand, are gradually introduced by means of 2 dip pipes, the orifice of which is situated close to the stirrer turbine, onto a heel (that is to say a mass already present in the reactor) brought to the desired temperature.

The amount of pTFMA introduced is 1 mol. The operating parameters and the results obtained are collated in the following table.

| Test No. | Temperature | Cl$_2$/pTFMA molar ratio | Duration of introduction of the chlorine | Duration of introduction of the substrate | Reaction yield | Degree of conversion |
|---|---|---|---|---|---|---|
| 1 | 115° C. ± 2 | 3.25 | 2 h | 2 h | ≧99% | 99.9% |
| 2 | 105° C. ± 2 | 3 | 2 h | 1 h ¾ | 86% | 100% |
| 3 | 105° C. ± 2 | 2.35 | 2 h 30 | 2 h | 82% | 100% |
| 4 | 80° C. ± 2 | 2.3 | 1 h 20 | 1 h 20 | 45% | 98% |
| 5 | 110° C. ± 2 | 2.5 | 3 h | 3 h | 94% | 99.5% |

The results obtained in this example are somewhat better than those of example 1 because of the side reactions during the rise in temperature.

What is claimed is:

1. A process for the preparation of an aniline compound chlorinated on the ring, and having at least one carbon atom of $sp^3$ hybridization, which is perhalogenated and carries a fluorine atom, said process comprising the step of chlorination of a precursor aniline compound, in a hydrofluoric acid medium capable of exchanging a chlorine atom and a fluorine atom in a benzyl position or on said carbon atom of $sp^3$ hybridization carrying a chalcogen atom, said precursor aniline compound being of the formula:

| Test No. | PTFMA · nHF | Cl$_2$ | T° | Duration | DC pTFMA | RY monochloro-pTFMA | RY dichloro-pTFMA | Comments |
|---|---|---|---|---|---|---|---|---|
| 1 | n = 4.5<br>m ≅ 10 g | 2.2 equivalents | 80° C. | 5 h | 95% | 1.5% | 19% | |
| 2 | n = 4.5<br>m ≅ 10 g | 2.6 equivalents | 110° C. | 6 h | 93% | 0.9% | 2.4% | |
| 3 | n = 4.5<br>m ≅ 10 g<br>+MCB ≅ 50%<br>by weight | 2.2 equivalents | 110° C. | 6 h | 60% | 0.6% | 0.8% | |
| 4 | No MCB | 2.1 equivalents | 80° C. | 5 h | 93.5% | 1.2% | 25% | |

MCB means monochlorobenzene

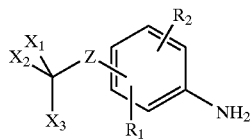

wherein:

Z represents a single bond or the chalcogen atom;

$X_1$, $X_2$, and $X_3$ represent identical or different halogens, with the further proviso that at least two halogens are other than fluorine; and $R_1$ and $R_2$ are halogens, alkyls, aryls or nitriles.

2. The process according to claim 1, wherein the chlorination step is carried out at a temperature of between 0 and 150° C.

3. The process according to claim 2, wherein the temperature is of between 20 and 120° C.

4. The process according to claim 1, wherein the chlorination step is carried out at atmospheric pressure or under autogenous pressure.

5. The process according to claim 1, wherein chlorine is gradually added by sparging into the medium.

6. The process according to claim 1, wherein chlorine is stoichiometrically added in excess so that the medium always remains chlorinating.

7. The process according to claim 5, wherein, as soon as sparging of chlorine ceases, the medium is suddenly cooled.

8. The process according to claim 7, wherein cooling is carried out, at least partially, by removing the hydrofluoric acid under reduced pressure.

9. The process according to claim 1, wherein the aniline precursor is the para-trifluoromethylaniline and the aniline compound chlorinated on the ring so obtained is the ortho-ortho'-dichloro-para-trifluoromethylaniline.

* * * * *